US011655440B2

(12) United States Patent
Russell et al.

(10) Patent No.: US 11,655,440 B2
(45) Date of Patent: May 23, 2023

(54) METHODS AND DEVICES FOR ASEPTIC DRY TRANSFER

(71) Applicant: CORNING INCORPORATED, Corning, NY (US)

(72) Inventors: Ryann Loren Russell, Drexel Hill, PA (US); Paul Kevin Seeto, Clinton, MA (US)

(73) Assignee: CORNING INCORPORATED, Corning, NY (US)

( * ) Notice: Subject to any disclaimer, the term of this patent is extended or adjusted under 35 U.S.C. 154(b) by 0 days.

(21) Appl. No.: 16/766,028

(22) PCT Filed: Nov. 26, 2018

(86) PCT No.: PCT/US2018/062470
§ 371 (c)(1),
(2) Date: May 21, 2020

(87) PCT Pub. No.: WO2019/108483
PCT Pub. Date: Jun. 6, 2019

(65) Prior Publication Data
US 2020/0354665 A1 Nov. 12, 2020

Related U.S. Application Data

(60) Provisional application No. 62/592,709, filed on Nov. 30, 2017.

(51) Int. Cl.
*B65D 41/04* (2006.01)
*C12M 1/12* (2006.01)
(Continued)

(52) U.S. Cl.
CPC ............ *C12M 25/16* (2013.01); *B65D 39/00* (2013.01); *B65D 41/00* (2013.01); *B65D 41/04* (2013.01);
(Continued)

(58) Field of Classification Search
CPC ........ C12M 23/38; B65D 83/06; B65D 45/30; B65D 45/305; B65D 41/0442;
(Continued)

(56) References Cited

U.S. PATENT DOCUMENTS

| 4,832,095 A | 5/1989 | Bonnell |
| 7,709,251 B2 | 5/2010 | Ellis et al. |

(Continued)

FOREIGN PATENT DOCUMENTS

| CA | 2833702 A1 | 6/2014 |
| CN | 201686685 U | 12/2010 |

(Continued)

OTHER PUBLICATIONS

International Search Report and Written Opinion of the International Searching Authority; PCT/US2018/062470; dated Feb. 20, 2019; 10 Pages; European Patent Office.

(Continued)

*Primary Examiner* — Allan D Stevens
(74) *Attorney, Agent, or Firm* — Michael G. Panian

(57) ABSTRACT

Devices and systems for product transfer, such as a dissolvable microcarriers, are described. In one example, the product delivery device may include an inlet port; a conical section that may include a wide end and a narrow end; an outlet port flush with the narrow end of the conical section and extending away from the conical section; and a securement feature configured to connect the wide end of the conical section to a container. In another example, a system for aseptic dry product delivery may include a container at least partially filled with the aseptic dry product; a product delivery device; a pressure source connected to an inlet port; and a receiving vessel where the aseptic dry product is collected.

7 Claims, 7 Drawing Sheets

(51) Int. Cl.
  *C12M 1/00* (2006.01)
  *B65D 39/00* (2006.01)
  *B65D 41/00* (2006.01)
  *B65D 41/16* (2006.01)
  *B65D 83/06* (2006.01)

(52) U.S. Cl.
  CPC ............. *B65D 41/16* (2013.01); *B65D 83/06* (2013.01); *C12M 23/38* (2013.01); *C12M 29/00* (2013.01)

(58) Field of Classification Search
  CPC ............ B65D 41/0435; B65D 41/0492; B65D 2543/00351; B65D 2543/0024; B65D 2543/00564; B65D 2543/00972
  See application file for complete search history.

(56) References Cited

U.S. PATENT DOCUMENTS

| | | | |
|---|---|---|---|
| 9,376,655 B2 | 6/2016 | Larsen et al. | |
| 2003/0155452 A1 | 8/2003 | Herget | |
| 2005/0282269 A1 | 12/2005 | Proulx | |
| 2008/0089967 A1* | 4/2008 | Bourque | B65D 45/305 425/190 |
| 2009/0212061 A1* | 8/2009 | Naesje | B29C 45/4407 220/714 |
| 2012/0197087 A1* | 8/2012 | Smith | H04L 41/026 600/208 |
| 2013/0030379 A1* | 1/2013 | Ingram | A61J 1/1475 604/218 |
| 2013/0233898 A1* | 9/2013 | Resnikoff | A47G 19/2272 222/568 |
| 2014/0263321 A1* | 9/2014 | Chisholm | B65D 51/145 220/240 |
| 2017/0292102 A1 | 10/2017 | Abraham et al. | |
| 2021/0277346 A1* | 9/2021 | Eidt | C12M 23/38 |

FOREIGN PATENT DOCUMENTS

| | | |
|---|---|---|
| CN | 203938032 U | 11/2014 |
| CN | 204624206 U | 9/2015 |
| CN | 204661734 U | 9/2015 |
| CN | 204846758 U | 12/2015 |
| CN | 105270727 A | 1/2016 |
| CN | 204958920 U | 1/2016 |
| CN | 105540033 A | 5/2016 |
| GB | 2463292 A | 3/2010 |
| JP | 04-089701 U | 8/1992 |
| JP | 2002-012296 A | 1/2002 |
| JP | 2002-034802 A | 2/2002 |
| JP | 2003-246462 A | 9/2003 |
| JP | 2005-212805 A | 8/2005 |
| JP | 2008-011757 A | 1/2008 |
| JP | 2011-251739 A | 12/2011 |
| JP | 5497944 B1 | 5/2014 |
| JP | 2014-117281 A | 6/2014 |
| JP | 2015-193392 A | 11/2015 |
| WO | 2016/188781 A1 | 12/2016 |
| WO | 2016/193150 A1 | 12/2016 |

OTHER PUBLICATIONS

Thomson Instrument Company, "Optimum Growth Transfer Caps", Available Online at <https://web.archive.org/web/20190421120226/https://htslabs.com/og/tc/>, Apr. 21, 2019, 14 pages.

Japanese Patent Application No. 2020-529237, Office Action, dated Oct. 26, 2022, 8 pages (4 pages of English Translation and 4 pages of Original Copy); Japanese Patent Office.

Chinese Patent Application No. 201880077860.1, Office Action dated Feb. 8, 2023, 5 pages (English Translation only), Chinese Patent Office.

* cited by examiner

METHODS AND DEVICES FOR ASEPTIC DRY TRANSFER

CROSS REFERENCE TO RELATED APPLICATION

This is a national stage application under 35 U.S.C. § 371 of International Application No. PCT/US2018/062470 filed on Nov. 26, 2018, which claims the benefit of priority under 35 U.S.C § 120 of U.S. Provisional Application Ser. No. 62/592,709 filed on Nov. 30, 2017, the contents of which are relied upon and incorporated herein by reference in their entirety.

BACKGROUND

The following relates generally to product transfer, and more specifically to transferring dry product in an aseptic system.

Products, such as dry powders, may be difficult to transfer out of a container based on the properties of the container. For example, dry powders may not completely transfer out of a system due to product hang up. Powders may get hung up on rough or flat surfaces, which leads to a loss of usable product. Dry powders, such as dissolvable microcarriers, may be transported in a sealed container to prevent contamination from the environment. In many cases, cell growth or regulatory standards may require a closed, aseptic, or sterile environment.

The deployment of dissolvable microcarriers in adherent cell cultures allows more surface area per unit volume for cell growth than two dimensional surfaces. Traditionally, cell growth within bioreactors was limited by the surface area available on traditional two-dimensional adherent surfaces. Microcarriers may have the ability to easily scale up cell growth within bioreactors. Dry microcarriers may have a substantially spherical shape with a diameter of about 30 microns. Once hydrated, microcarriers may have a diameter of about 250 microns.

Complete product transfer may be significant for the cost and yields desired by a consumer. Product that remains in the container may be unusable and can result in the loss of money and a lower process yield. To enable increased product transfer in systems such as aseptic cell cultures with microcarriers, an aseptic transfer device may be needed to introduce product (e.g., the microcarriers) into the system (e.g., culture vessel).

SUMMARY

The present disclosure is directed towards a device and systems for product delivery. In some embodiments, the product delivery device can include an inlet port, a conical section including a wide end and a narrow end, an outlet port flush with the narrow end of the conical section and extending away from the conical section, and a securement feature configured to connect the wide end of the conical section to a container.

In some embodiments, the diameter of the narrow end is smaller than the diameter of the wide end. In some embodiments, walls of the conical section extend from the wide end to the narrow end and can define an angle of the conical section. In some cases, the angle of the conical section can vary along a circumference of the narrow end, the wide end, or both. In other cases, the angle of the conical section can be uniform along a circumference of the narrow end, the wide end, or both.

In some embodiments, the device or system can further include a single piece cap that can include the inlet port, the conical section, the outlet port, and the securement feature. According to various aspects of the disclosure, the securement feature can be configured to form a wedge fit with the container. In some cases, the cap can be formed by injection molding.

In some embodiments, the device or system can further include a two-piece cap that can include the inlet port, the conical section, the outlet port, and the securement feature. According to various aspects of the disclosure, the device or system can also include a first piece comprising a stopper, and a second piece comprising the securement feature, wherein the first piece can engage with the second piece to create a seal when connected to the container.

In some embodiments, the device or system can further include a three or more-piece cap including the inlet port, the conical section, the outlet port, and the securement feature. According to various aspects of the disclosure, the device or system can also include a first piece including the conical section and the outlet port, a second piece including the securement feature, and a third piece including a gasket, wherein the first piece engages with the second piece to deform the gasket when connected to the container.

In some embodiments, the gasket can include an internal angle based at least in part on an angle of the conical section. In some embodiments, the securement feature includes threads configured to engage an internal surface of the container.

In some embodiments, the product delivery device can include at least one of polyethylene, polypropylene, polystyrene, polycarbonate, or silicon. In some embodiments, the inlet port and outlet port include an external barb.

A system for product delivery can include a container at least partially filled with the product, and a product delivery device including a conical section with a wide end and a narrow end, and an outlet port flush with the narrow end of the conical section, wherein the product is transferred from the conical section through the outlet port.

In some embodiments, the device or system can further include an inlet port, and a securement feature configured to connect the wide end of the conical section to the container. According to various aspects of the disclosure, the device or system can also include a dip tube connected to the inlet port and extending to an opposite side of the container that the inlet port.

In some embodiments, the device or system can further include a gasket between the product delivery device and the container, the gasket configured to deform to create a hermetic seal. In some embodiments, the device or system can be aseptic.

In some embodiments, the product is a dry free flowing powder. In some cases, the product is dissolvable microcarriers.

Another system for product delivery can include a container at least partially filled with the aseptic dry product, a product delivery device including a conical section with a wide end and a narrow end, and an outlet port flush with the narrow end of the conical section. According to his system, the dry product is transferred from the conical section through the outlet port, a pressure source connected to an inlet port, and a receiving vessel, where the aseptic dry product is collected.

In some embodiments, the device or system can further include a gasket between the product delivery device and the container, the gasket being configured to deform to create a hermetic seal. In some embodiments, the device or system can be closed to the environment. In some embodiments, the device or system can be aseptic or sterile.

In some embodiments, the device or system can further include a dip tube connected to the inlet port that extends into the container. The dip tube can be configured to transfer pressure from the pressure source into the container.

In some embodiments, the product is a dry, free-flowing powder. In some cases, the product includes dissolvable microcarriers. In some examples, the dry product can be hydrated in the receiving vessel. In some embodiments, the inlet port and outlet port include an external barb.

In some embodiments, the device or system can further include a first tube connected to the inlet port, a first clamp configured to pinch the first tube, a second tube connected to the outlet port, and a second clamp configured to pinch the second tube.

One or more representative embodiments is provided to illustrate the various features, characteristics, and advantages of the disclosed subject matter. The embodiments are provided in the context of glass electrochemical sensors. It should be understood, however, that many of the concepts can be used in a variety of other settings, situations, and configurations. For example, the features, characteristics, advantages, etc., of one embodiment can be used alone or in various combinations and sub-combinations with one another.

The Summary is provided to introduce a selection of concepts in a simplified form that are further described below in the Detailed Description. The Summary and the Background are not intended to identify key concepts or essential aspects of the disclosed subject matter, nor should they be used to constrict or limit the scope of the claims. For example, the scope of the claims should not be limited based on whether the recited subject matter includes any or all aspects noted in the Summary and/or addresses any of the issues noted in the Background.

BRIEF DESCRIPTION OF DRAWINGS

The preferred and other embodiments are disclosed in association with the accompanying drawings in which.

DETAILED DESCRIPTION

The present disclosure relates to devices and systems for delivering materials (e.g., dry products) wherein the devices and systems enable as complete of a transfer as possible, including, but in no way limited to, the aseptic transfer of dissolvable microcarriers (DMCs). An easy to use container can enable the optimal delivery of product while minimizing the product lost, which can be hung up in the container (e.g., the lid and outlet port of the container). Such a device can be valuable for systems that require specific environmental standards, such as a clean room, to avoid contamination. The transfer can enable the system to remain closed to the outside environment, allowing reduced requirements for the external environment of the system. In some cases, product that is sterile or aseptic could remain sterile or aseptic using the devices and systems described herein. The devices and systems described can also be designed to withstand abnormal pressure (e.g., above or below atmospheric pressure). A pressure gradient in combination with the described devices and systems can allow a more complete delivery of product. In some cases, the product to be delivered by this device can be dry or wet, and the product can be a fluid or a solid.

Conventional systems for delivering materials (e.g., dry products) can be unable to minimize the residual material in a container due to the geometry of such devices. The present disclosure relates to a product delivery system that enables improved product transfer by reducing resistance of the path for a product to exit the container in the system, which allows for minimized product hang up. This disclosure lends itself to the transfer of DMCs in a closed system, thus enabling the process of adherent cell growth in a bioreactor. In particular, this system can include a container at least partially filled with product (e.g., aseptic dry DMCs), and a cap device that connects to the container. In some examples, this process also allows for the use of back pressure to force more product out of the container and allows for a more rapid flow out of the container, relative to the use of gravity alone, and through any associated tubing. The product can leave the container through an outlet port that is flush with a narrow end of a conical section. The outlet port may not extend into the conical section, which reduces the resistance of the path for a product to exit the container. Although this disclosure can be described in relation to the transfer of DMCs, the devices and systems can be applied to the transfer of a variety of materials.

Figure 1:
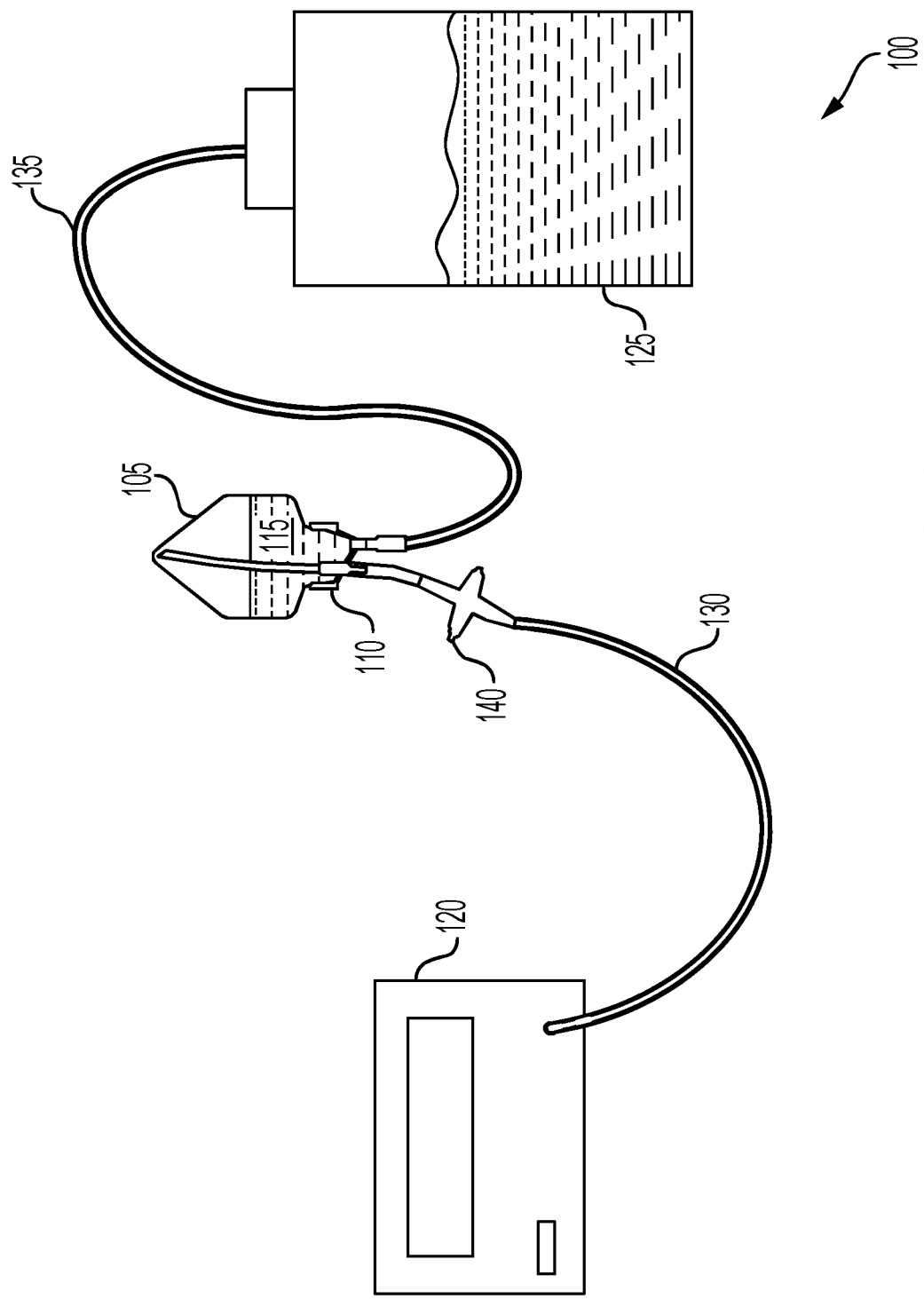
FIG. 1 illustrates a cross-sectional view of an example of a closed system for product transfer in accordance with various aspects of the present disclosure.

FIG. 1 illustrates a cross-sectional view of an example of a closed system 100 for product transfer in accordance with various aspects of the present disclosure. As illustrated in FIG. 1, the system 100 can include a container 105, a product delivery device 110, a pressure source 120, and a receiving vessel 125.

The container 105 can be at least partially filled with a product 115 (e.g., a free-flowing powder such as dry DMCs). The container 105, as shown in FIG. 1, is inverted. Before the container 105 is inverted, a dip tube can be inserted in the inlet port, the product delivery device 110 (e.g., a cap) can be secured onto the container 105, and the tubing 130 and 135 can be connected to the inlet port and outlet port, respectively. The container 105 can be secured in an inverted position by a clamp or other commonly known configurations for positioning a device.

The product delivery device 110 can be secured onto the container 105 (e.g., screwing onto internal or external threads on the container), formed as an integral part of the container 105 by any number of manufacturing methods, including, but in no way limited to, 3D printing, blow molding, and the like. The product delivery device 110 can have a conical internal shape, where internal is defined herein as being disposed between the walls of the device 110. The conical section of the product delivery device 110 can allow for optimized transfer of product 115 to the receiving vessel 125 by reducing residual product in the container 105.

The pressure source 120 can be connected to the inlet of the product delivery device 110 by tubing 130, which can include a vent 140 and vent filter to catch or otherwise prevent contaminates from entering the container 105. Alternatively, the vent 140 can be attached to the container 105, rather than the tubing 130. In any event, the tubing 130 and vent 140 form a fluid flow path between the pressure source 120 and the inlet of the container 105. The pressure source 120 can provide pressure through the tubing 130 to the dip tube in the container 105 in order to provide pressure at the top of the container 105. As illustrated in FIG. 1, the top of the container 105 is shown with no product 115. Consequently, the addition of pressure to the container 105 can apply a force on the product 115 to move to a lower pressure area (e.g., the receiving vessel 125). Thus, the product 115 will travel out of the container 105 and have minimal, if any, product hang up in the container 105 due to the shape of the conical section and the placement of the outlet port.

Receiving vessel 125 can be connected to the outlet of the product delivery device 110 by tubing 135. In some examples, the receiving vessel 125 can be a bioreactor where the product 115 transferred from the container 105 can aid in cell growth. If the product 115 were DMCs, then the DMCs can be hydrated within the receiving vessel 125.

The entire system 100 can be closed and be configured to maintain an aseptic or sterile environment. The size of the container 105, product delivery device 110, and other aspects of the system 100 can be a variety of sizes, based on the amount of the product 115.

Figure 2:
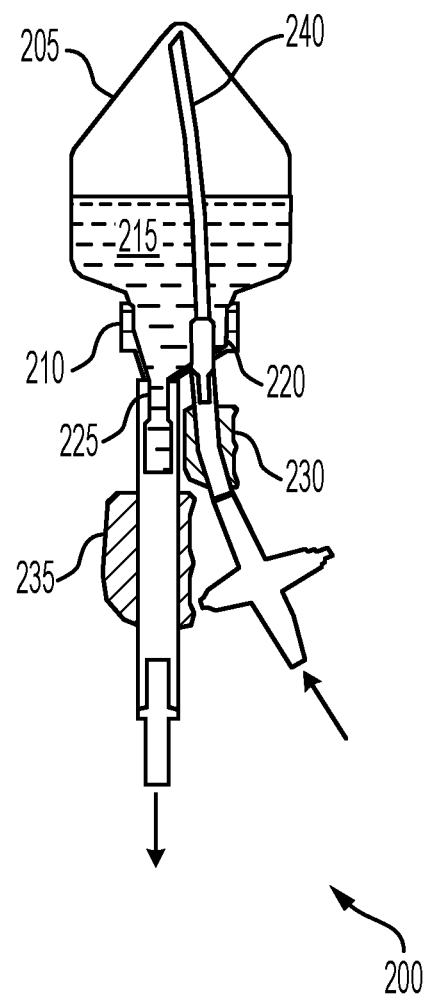
FIG. 2 illustrates a cross-sectional view of an example of a product delivery system in accordance with various aspects of the present disclosure.

FIG. 2 illustrates a cross-sectional view of an example of a product delivery system 200 in accordance with various aspects of the present disclosure. As illustrated in FIG. 2, the system 200 can include a container 205, a product delivery device 210, product 215, an inlet port 220, and an outlet port 225. The container 205 can be an example of container 105 as shown in FIG. 1. Product delivery device 210 can be an example of product delivery device 110.

The inlet port 220 of the product delivery device 210 can be connected to a dip tube 240 that extends from the inlet port 220 to the opposite side of the container 205 (e.g., the top of the container 205). A pressure source (120 from FIG. 1) can be connected to the inlet port 220 outside of the container 205 and can provide pressure through the dip tube 240 into the container 205 in order to provide pressure at the top of the container 205 where the top of the container 205 is shown with no product 215. The addition of pressure to the container 205 can apply a force on the product 215 to move to a lower pressure area. Thus, the product 215 will travel out of the container 205 and have minimal if any product hang up in the container 205 due to the shape of the conical section and the placement of the outlet port 225.

In some cases, the tubing that is fluidly connected to the inlet port 220 can include a clamp 230. The clamp 230 can temporarily engage the tubing (e.g., tubing 130 in FIG. 1) to create a pinch in the tubing to prevent product 215 from flowing further into the tubing. Another clamp 235 can be placed on tubing that is fluidly connected to the outlet port 225. Clamp 235 can be similar to clamp 230, and clamp 235 can temporarily engage the tubing (e.g., tubing 135 in FIG. 1) to create a pinch in the tubing to prevent product 215 from flowing further into the tubing. Once the system is ready for operation, the clamps 230 and 235 can be disengaged to allow product, pressurized air, or other elements to flow through the tubing. For example, the clamps 230 and 235 can be disengaged after tubing on the far side of the clamp, the side opposite the outlet port 225, is welded to other tubing in the system and evacuated of any undesirable elements. These clamps 230 and 235 can allow for cleaner tube welds and for maintaining the seal of the system 200 from the external environment. Thus, the system 200 can remain closed.

According to various aspects of this disclosure, the outlet port 225 can be arranged on the product delivery device 210 such that the uppermost portion of the outlet port 225 is flush with the interior conical section of the container 205. For example, the edge between the conical section and the outlet port 225 can be continuous and smooth such that there is reduced resistance for a product 215 to exit the container 205 through the outlet port 225.

Figure 3:
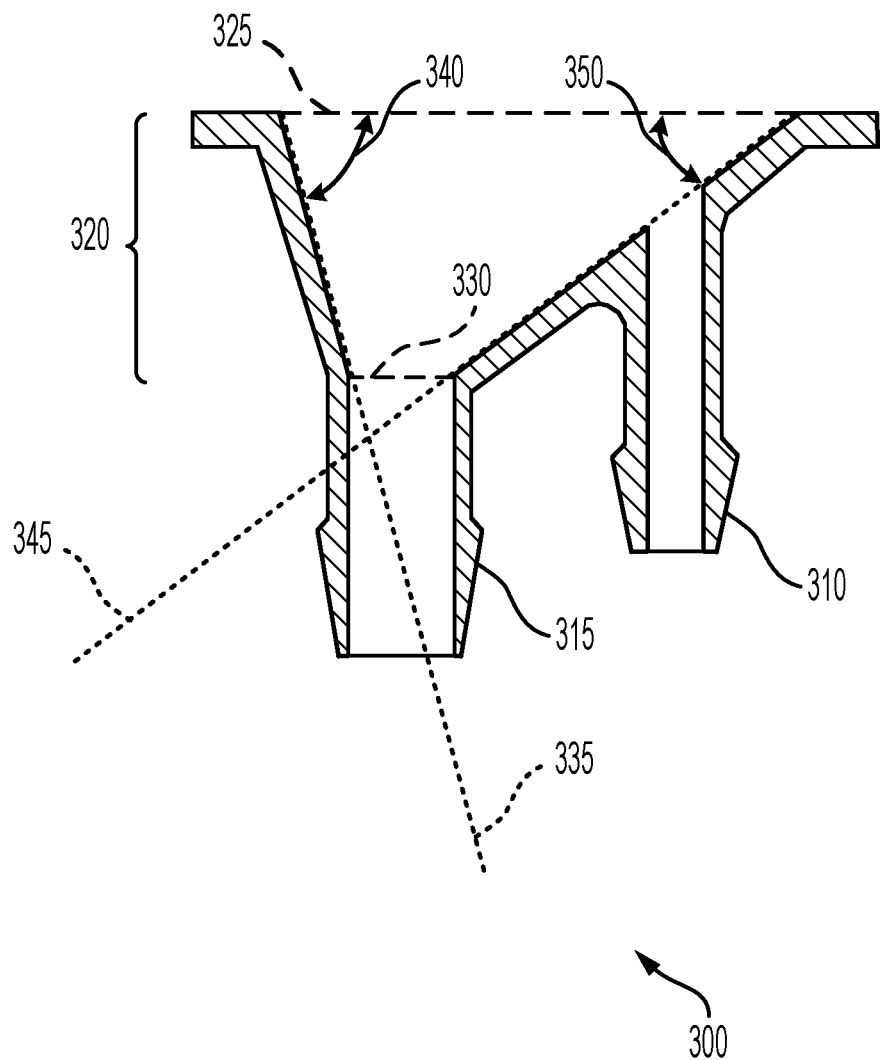
FIG. 3 illustrates a cross-sectional view of an example of a product delivery device in accordance with various aspects of the present disclosure.

FIG. 3 illustrates a cross-sectional view of an example of a product delivery device 300, in accordance with various aspects of the present disclosure. As illustrated in FIG. 3, the product delivery device 300 can include an inlet port 310, an outlet port 315, and a conical section 320.

Inlet port 310 can be arranged anywhere on the device 300 apart from and physically separated from the outlet port 315. In some examples, the inlet port 310 can be connected to the conical section 320 at a distance from the outlet port 315. As illustrated in FIG. 3, the inlet port 310 can be flush with the conical section 320. In other cases, the inlet port 310 can extend into the conical section 320 and can include a dip tube disposed therein.

The outlet port 315 can be attached to the narrow end 330 of the conical section. The outlet port 315 can be flush with the conical section 320 (e.g., a continuous surface with a corner). The outlet port 315 can be positioned anywhere on the device 300 provided that the outlet port 315 is flush with the narrow end of the conical section.

Conical section 320 can also include a wide end 325 and a narrow end 330. The narrow end 330 can have a diameter that is smaller than the diameter of the wide end 325. Dotted lines 335 and 345 are shown to clarify the angles of the conical section 320 walls. Angles 340 and 350 are depicted between the plane of the wide end 325 and dotted lines 345 and 355, respectively. Angles 340 and 350 can be different or the same. If the angles 340 and 350 are different, the angles around the entire conical section can vary along the circumference of the wide end 325, the narrow end 330, or both. If the angles 340 and 350 are the same, the angles around the entire conical section can be uniform along the circumference of the wide end 325 and the narrow end 330. Angles 340 and 350 can be greater than 0 degrees, for example greater than 25 degrees.

Figure 4:
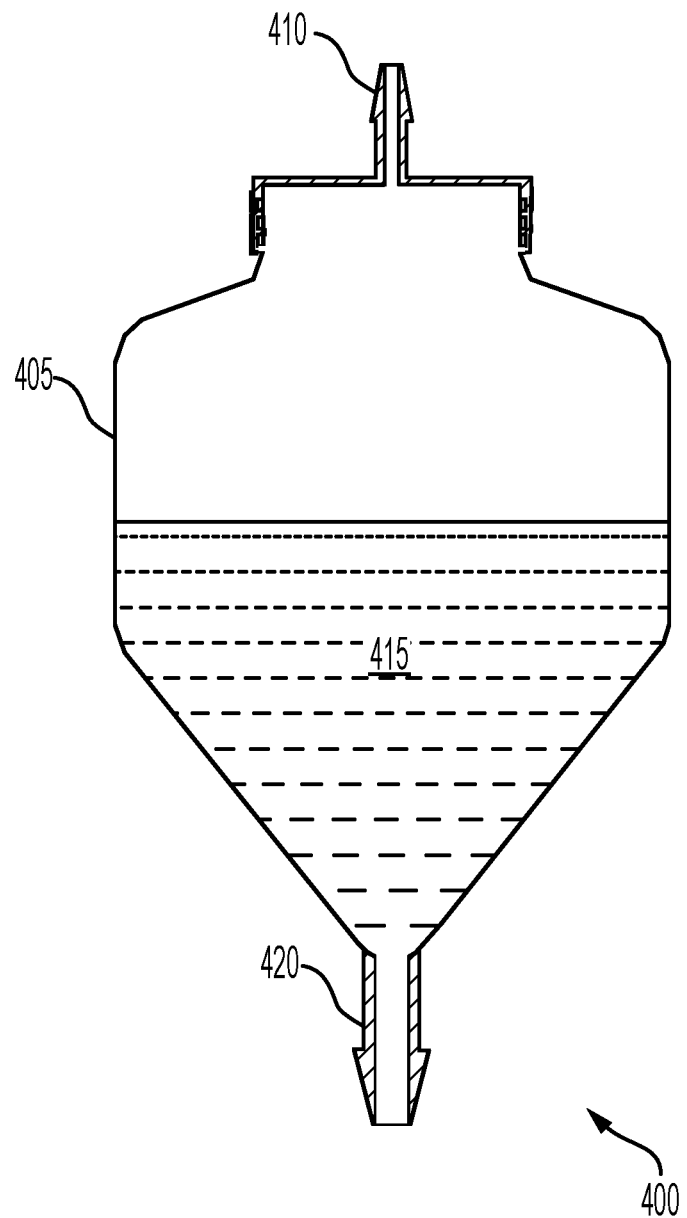
FIG. 4 illustrates a cross-sectional view of an example of an alternative product delivery system in accordance with various aspects of the present disclosure.

FIG. 4 illustrates a cross-sectional view of an example of an alternative product delivery system 400 in accordance with various aspects of the present disclosure. As illustrated in FIG. 4, system 400 can include a container 405, inlet port 410, and outlet port 420. This system 400 can be implemented in system 100.

Container 405 can be at least partially filled with product 415. In some cases, container 405 can have a conical shape as illustrated in FIG. 4.

Inlet port 410 can be secured to the top of the container 405. In some examples, inlet port 410 can allow pressure to be transferred into the container 405 to apply a pressure to the product 415. The pressure can force the product 415 out of the container 405 through the outlet port 420.

Outlet port 420 can be connected to the conical section of the container 405. The outlet port 420 can be flush with the narrow end of the conical section of the container 405.

Figure 5:
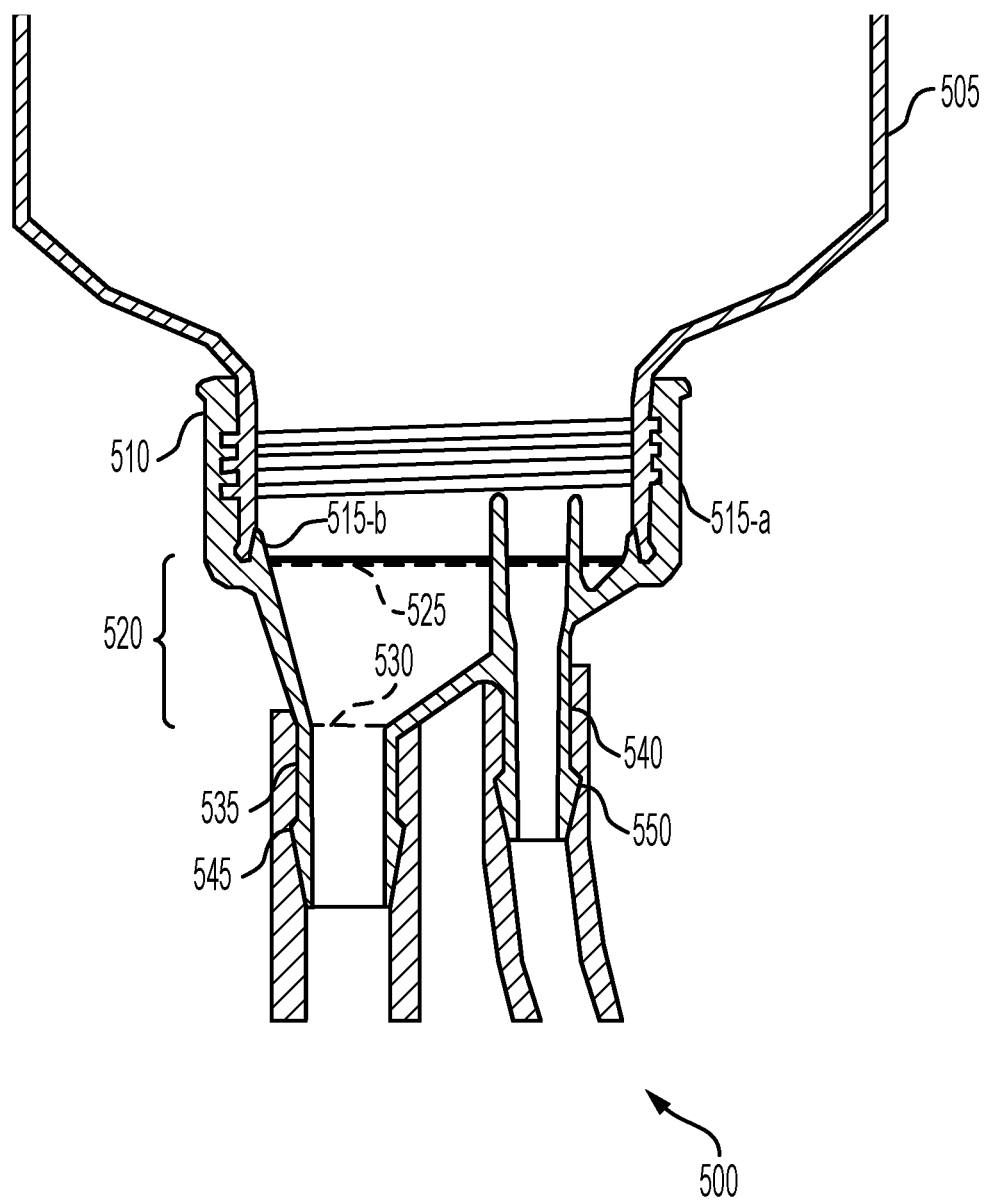
FIG. 5 illustrates a cross-sectional view of an example of a single piece product delivery system in accordance with various aspects of the present disclosure.

FIG. 5 illustrates a cross-sectional view of an example of a single piece product delivery system 500, in accordance with various aspects of the present disclosure. As illustrated in FIG. 5, system 500 can include a container 505 and a product delivery device 510.

Product delivery device 510 can be a single piece of material that includes securement features 515, a conical section 520, an outlet port 535, and an inlet port 540. Product delivery device 510 can be formed by any number of manufacturing methodologies including, but in no way limited to, injection molding. In some examples, the product delivery device 510 can be manufactured of any suitable material, including, but in no way limited to, at least one of polyethylene, polypropylene, polystyrene, polycarbonate, or silicone.

Securement features 515-a and 515-b can attach the wide end 525 of the conical section 520 to the container 505. In some cases, securement feature 515-a can engage with threads of the container 505. As shown, the securement features 515-a of the container 505 are illustrated as external threads formed as circumferential protrusions on the lower outer surface of the container 505 adjacent to the bottom-most opening in the container, where they can be rotationally engaged with internal threads formed on the inner circumferential surface of the product delivery device. However, in some cases, the securement feature 515-a can engage with internal threads of the container 505. Securement feature 515-b can form a wedge or interference fit with the inside or top of the container mouth. The securement features 515-b can have an internal angle similar in geometry to the conical section 520 to allow smooth flow of product. The securement features 515-a and 515-b allow for an improved seal between the product delivery device 510 and the container 505. In some cases, the seal can allow the system 500 to be closed.

Conical section 520 can include a wide end 525 and a narrow end 530. An outlet port 535 can be flush with the narrow end 530. As illustrated, outlet port 535 and inlet port 540 can include one or more external barbs 545 and 550, respectively. Barbs 545 and 550 allow for tubing to securely connect to each port. In some cases, the barbs 545 and 550 allow tubing to remain connected to the ports when the system is pressurized.

Figure 6:
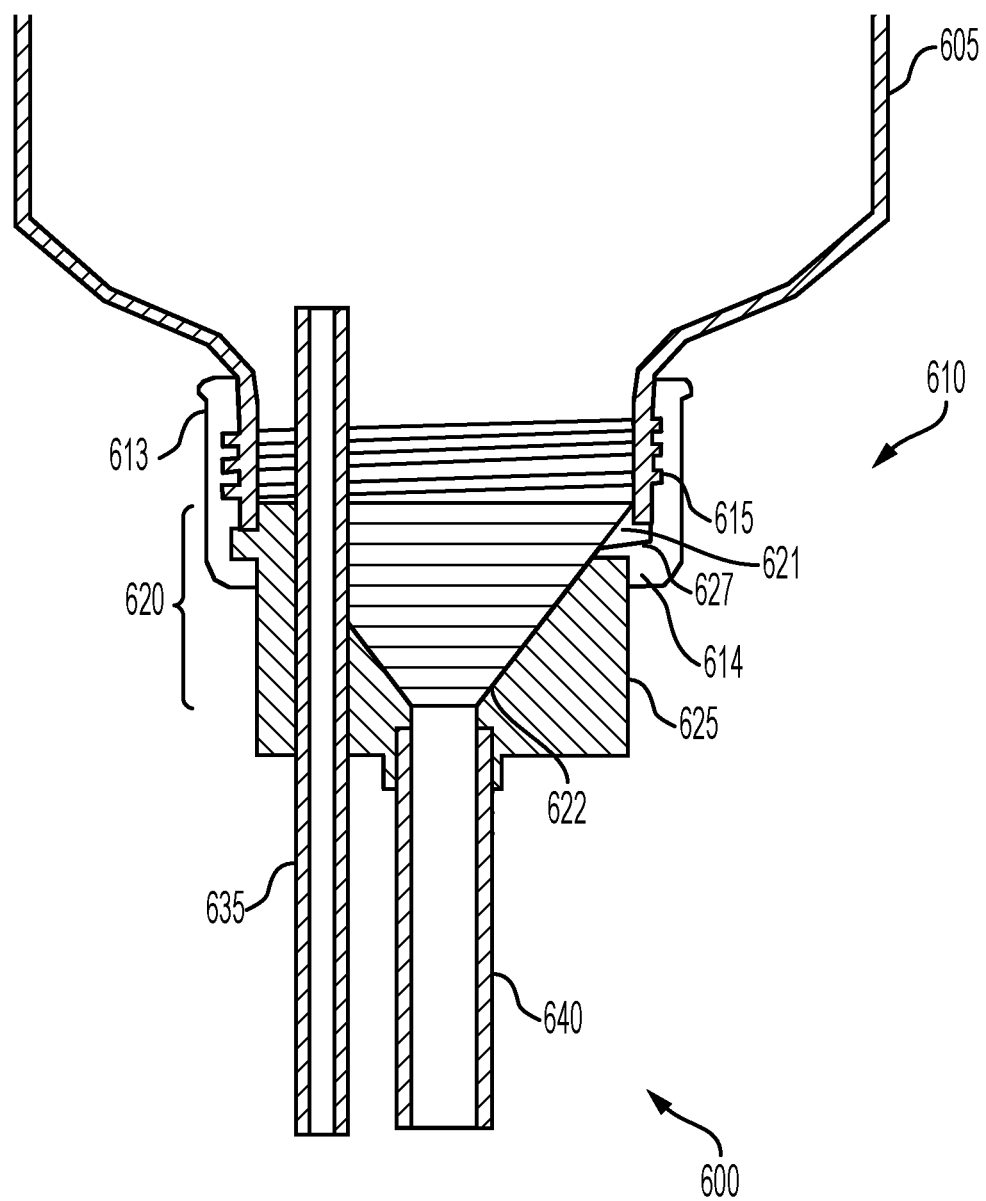
FIG. 6 illustrates a cross-sectional view of an example of a two-piece product delivery system in accordance with various aspects of the present disclosure.

FIG. 6 illustrates a cross-sectional view of an example of a two-piece product delivery system 600 in accordance with various aspects of the present disclosure. As illustrated in FIG. 6, system 600 can include a container 605 and a two-piece product delivery device 610.

Product delivery device 610 can be two separate component pieces, combined to form the delivery device 610. The first piece can include a collar piece 613 including a distal lip 614, having the securement features 615 formed on an inner surface of the collar piece 613, as illustrated in FIG. 6. The second piece of the product delivery device 610 can include the conical section 620, a stopper 625 including a seating lip 627 that engages the distal lip 614 of the collar piece 613, an inlet port 635, and an outlet port 640. In some examples, the product delivery device 610 can be formed of at least one or more of polyethylene, polypropylene, polystyrene, polycarbonate, or silicone.

Securement features 615 can attach the wide end of the conical section 620 to the container 605. In some cases, securement feature 615 can engage with threads of the container 605. As shown, the threads are formed as protrusions circumferentially formed on the external wall of the bottommost opening of the container 605, however, in some cases, the securement feature 615 can engage with internal threads of the container 605. When the securement features 615 of the first piece, such as the collar 613, engage with the threads of the container 605, the second piece can be positioned between the first piece and the container's mouth such that the edges of the stopper 625 are secured. More specifically, according to one embodiment, the seating lip 627 of the stopper 625 engages the distal lip 614 of the collar piece 613, and is compressed between the distal lip 614 of the collar piece and the end of the container 605 as it is advanced along the securement features. This configuration allows for a compressed seal between the product delivery device 610 and the container 605. In some cases, the seal can allow the system 600 to be closed.

Conical section 620 can include a wide end 621 and a narrow end 622, which can be hollowed out of the stopper 625. Stopper 625 can be made of a flexible material (e.g., silicone), and the collar piece 613 can be made of a rigid material (e.g., polyethylene). The angle of the conical section 620 can be the same or differ along the circumference of the wide end 621, the narrow end 622, or both. If the angles are the same around the entire conical section, they can be uniform along the circumference of the wide end and the narrow end, as shown. In some cases, the angles can be greater than 0 degrees, for example greater than 25 degrees.

An outlet port 640 can be flush with the narrow end of the conical section 620. As illustrated, inlet port 635 and outlet port 640 can extend away from the container 605. The outlet port 640 can be centered within the stopper 625. Although not shown, the inlet port 635 and outlet port 640 can include external barbs.

Figure 7:
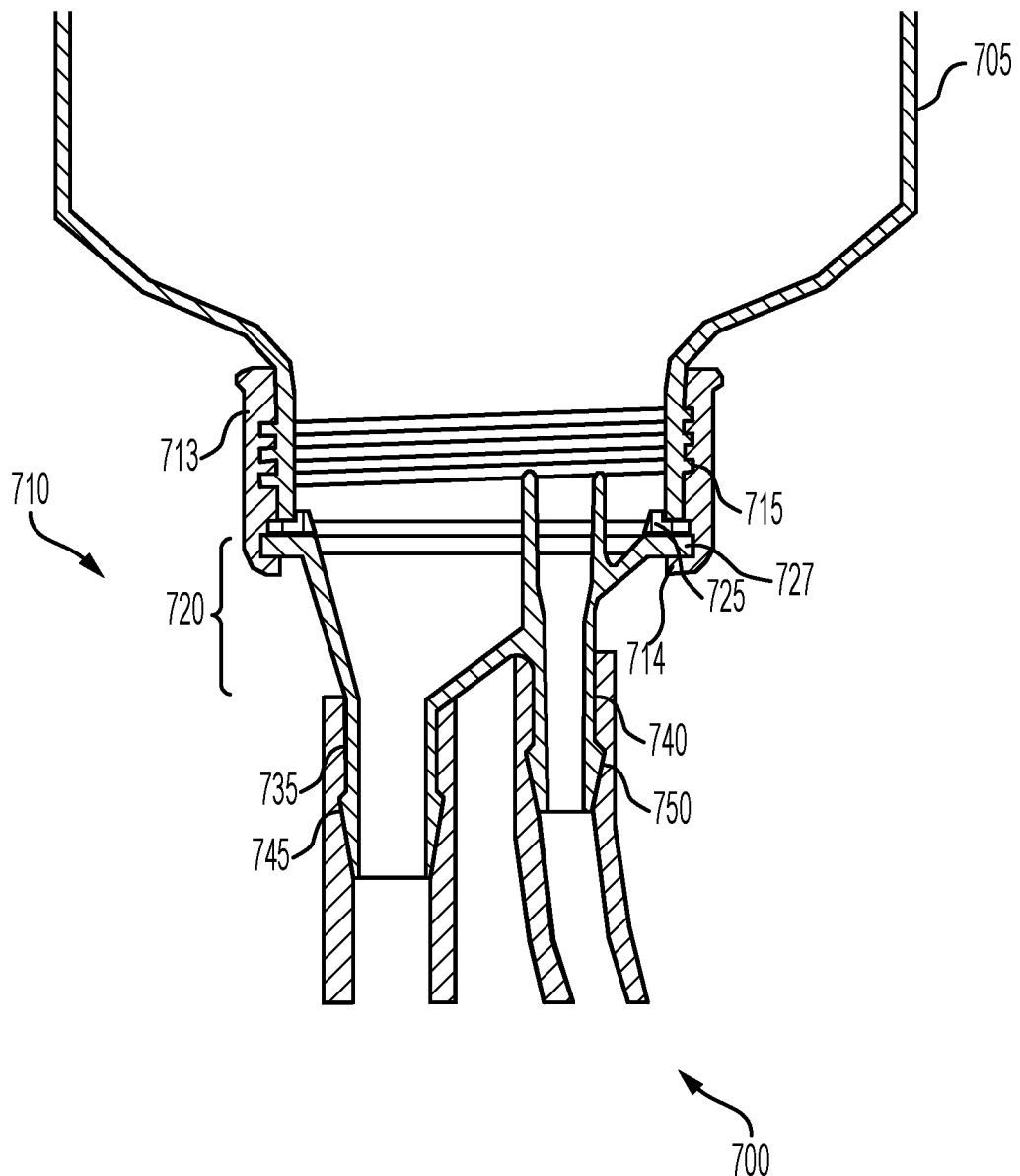
FIG. 7 illustrates a cross-sectional view of an example of a three-piece product delivery system in accordance with various aspects of the present disclosure.

FIG. 7 illustrates a cross-sectional view of an example of a three-piece product delivery system 700 in accordance with various aspects of the present disclosure. As illustrated in FIG. 7, the system 700 can include a container 705 and a three-piece product delivery device 710.

The three-piece product delivery device 710 can be formed of three separate and distinct pieces, which can be manufactured of the same or different types of material. The first piece of the three-piece product delivery device 710 can include a collar piece 713 including a distal lip 714, and a securement feature 715 formed on an inner surface thereof, as illustrated in FIG. 7. The second piece of the three-piece product delivery device 710 can include conical section 720, an outlet port 735, and an inlet port 740. As illustrated in FIG. 7, the second piece includes a seating lip 727 formed on an upper periphery of the conical section 720, the seating lip 727 being configured to interface with the distal lip 714 of the collar piece 713 when assembled. The third piece of the three-piece product delivery device 710 can include a gasket 725. As illustrated in FIG. 7, the gasket 725 engages the seating lip 727 of the second piece and is compressed between the top end of the container 705, the seating lip 727 of the conical section 720, and the distal lip 714 of the collar piece 713. In some examples, the product delivery device 710 can be manufactured of any combination of materials including, but in no way limited to, polyethylene, polypropylene, polystyrene, polycarbonate, and/or silicone.

As illustrated in FIG. 7, securement features 715 can operate to secure the wide end of the conical section 720 to the container 705. In some cases, securement feature 715 can engage with threads of the container 705. As shown, the threads are formed as protrusions circumferentially formed on the external wall of the bottommost opening of the container, however, in some cases, the securement feature 715 can engage with internal threads of the container 705. When the securement features 715 of the collar 713 engage with the threads of the container 705, the seating lip 727 of the second piece and the gasket 725 of the third piece can be positioned between the distal lip 714 of the collar 713 of the first piece and the mouth of the container 705, such that the intermediate elements are compressed, thereby sealing the interface between the various pieces. The gasket 725 can be made of a flexible material that can be deformed when force is added. The gasket 725 in the system 700 can be deformed to create a seal between the container 705 and the conical section 720. The gasket 725 can have an internal angle similar in geometry to the conical section 720 to allow smooth flow of product. The securement features 715 and gasket 725 allow for an improved seal between the product delivery device 710 and the container 705. In some cases, the seal can allow the system 700 to be closed.

The conical section 720 can include a wide end and a narrow end. An outlet port 735 can be flush with the narrow end. As illustrated, the outlet port 735 and the inlet port 740 can include one or more external barbs 745 and 750, respectively. Barbs 745 and 750 allow for tubing to securely connect to each port. In some cases, the barbs 745 and 750 can be important when the system is pressurized to allow tubing to remain connected to the ports.

According to an aspect (1) of the present disclosure, a product delivery device is provided. The product delivery device comprises: an inlet port; a conical section including a wide end and a narrow end; an outlet port disposed flush with the narrow end of the conical section extending away from the conical section; and a securement feature formed on the product delivery device, wherein the securement feature is configured to couple the wide end of the conical section to a container.

According to an aspect (2) of the present disclosure, the product delivery device of aspect (1) is provided, wherein the diameter of the narrow end is smaller than the diameter of the wide end.

According to an aspect (3) of the present disclosure, the product delivery device of aspect (2) is provided, wherein walls of the conical section extend from the wide end to the narrow end and define an angle of the conical section.

According to an aspect (4) of the present disclosure, the product delivery device of aspect (4) is provided, wherein, wherein the angle of the conical section varies along a circumference of the narrow end or the wide end.

According to an aspect (5) of the present disclosure, the product delivery device of aspect (3) is provided, wherein the angle of the conical section is uniform along a circumference of the narrow end or the wide end.

According to an aspect (6) of the present disclosure, the product delivery device of any of aspects (1)-(5) is provided, further comprising a single piece cap including the inlet port, the conical section, the outlet port, and the securement feature.

According to an aspect (7) of the present disclosure, the product delivery device of aspect (6) is provided, wherein, wherein the securement feature is configured to form a compression fit with the container.

According to an aspect (8) of the present disclosure, the product delivery device of aspect (6) is provided, wherein the cap is formed by injection molding.

According to an aspect (9) of the present disclosure, the product delivery device of any of aspects (1)-(8) is provided, further comprising a two-piece cap including the inlet port, the conical section, the outlet port, and the securement feature.

According to an aspect (10) of the present disclosure, the product delivery device of aspect (9) is provided, further comprising: a first piece including a stopper; and a second piece including the securement feature, wherein the first piece engages with the second piece to create a seal when connected to the container.

According to an aspect (11) of the present disclosure, the product delivery device of any of aspects (1)-(10) is provided, further comprising a three-piece cap including the inlet port, the conical section, the outlet port, and the securement feature.

According to an aspect (12) of the present disclosure, the product delivery device of aspect (11) is provided, further comprising: a first piece comprising the inlet port, the conical section and the outlet port; a second piece comprising the securement feature; and a third piece comprising a gasket, wherein the first piece engages with the second piece to deform the gasket when connected to the container.

According to an aspect (13) of the present disclosure, the product delivery device of aspect (12) is provided, wherein the gasket comprises an internal angle based at least in part on an angle of the conical section.

According to an aspect (14) of the present disclosure, the product delivery device of any of aspects (1)-(13) is provided, wherein the securement feature comprises threads configured to engage an external surface of the container.

According to an aspect (15) of the present disclosure, the product delivery device of any of aspects (1)-(14) is provided, wherein the product delivery device comprises at least one of polyethylene, polypropylene, polystyrene, polycarbonate, or silicone.

According to an aspect (16) of the present disclosure, the product delivery device of any of aspects (1)-(15) is provided, wherein the inlet port and outlet port comprise an external barb.

According to an aspect (17) of the present disclosure, a system for product delivery is provided. The system for product delivery comprises: a container; and a product delivery device comprising: a conical section with a wide end and a narrow end; and an outlet port flush with the narrow end of the conical section, wherein the product is transferred from the conical section through the outlet port.

According to an aspect (18) of the present disclosure, the system for product delivery of aspect (17) is provided, further comprising: an inlet port; and a securement feature configured to connect the wide end of the conical section to the container.

According to an aspect (19) of the present disclosure, the system for product delivery of aspect (18) is provided, further comprising a dip tube connected to the inlet port and extending into the container to a side opposite the inlet port.

According to an aspect (20) of the present disclosure, the system for product delivery of aspect (18) is provided, further comprising a gasket between the product delivery device and the container, the gasket configured to deform to create a hermetic seal.

According to an aspect (21) of the present disclosure, the system for product delivery of any of aspects (17)-(20) is provided, wherein the container further comprises a product, the product including a dry free flowing powder.

According to an aspect (22) of the present disclosure, the system for product delivery of aspect (21) is provided, wherein the product comprises dissolvable microcarriers.

According to an aspect (23) of the present disclosure a system for aseptic dry product delivery is provided. The system for aseptic dry product delivery comprises: a container; a product delivery device including: a conical section with a wide end and a narrow end; and an outlet port disposed flush with the narrow end of the conical section, wherein the dry product is transferred from the conical section through the outlet port; a pressure source connected to an inlet port; and a receiving vessel configured to receive the aseptic dry product.

According to an aspect (24) of the present disclosure, the system for product delivery of aspect (23) is provided, further comprising a gasket disposed between the product delivery device and the container, the gasket configured to deform to create a hermetic seal within the system.

According to an aspect (25) of the present disclosure, the system for product delivery of any of aspects (23)-(24) is provided, wherein the system is closed to the environment.

According to an aspect (26) of the present disclosure, the system for product delivery of any of aspects (23)-(25) is provided, wherein a dip tube connected to the inlet port extends into the container, and wherein the dip tube is configured to transfer pressure from the pressure source into the container.

According to an aspect (27) of the present disclosure, the system for product delivery of any of aspects (23)-(26) is provided, wherein the inlet port and outlet port comprise an external barb.

According to an aspect (28) of the present disclosure, the system for product delivery of any of aspects (23)-(27) is provided, further comprising: a first tube connected to the inlet port; a first clamp configured to pinch the first tube; a second tube connected to the outlet port; and a second clamp configured to pinch the second tube.

According to an aspect (29) of the present disclosure, the system for product delivery of any of aspects (23)-(28) is provided, wherein the container is at least partially filled with an aseptic dry product, the dry product comprising dissolvable microcarriers.

According to an aspect (30) of the present disclosure, the system for product delivery of aspect (29) is provided, wherein the dry product is hydrated in the receiving vessel.

It should be appreciated that some components, features, and/or configurations can be described in only one embodiment, but these same components, features, and/or configurations can be applied or used in or with many other embodiments and should be considered applicable to the other embodiments, unless stated otherwise or unless such a component, feature, and/or configuration is technically impossible to use with the other embodiment. Thus, the components, features, and/or configurations of the various embodiments can be combined in any manner and such combinations are expressly contemplated and disclosed by this statement.

The terms recited in the claims should be given their ordinary and customary meaning as determined by reference to relevant entries in widely used general dictionaries and/or relevant technical dictionaries, commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used in a manner that is more expansive than its ordinary and customary meaning, the term should be given its ordinary and customary meaning plus the additional expansive meaning, or (b) if a term has been explicitly defined to have a different meaning by reciting the term followed by the phrase "as used in this document shall mean" or similar language (e.g., "this term means," "this term is defined as," "for the purposes of this disclosure this term shall mean," etc.).

In this disclosure, the term "closed system" can refer to a system that is sealed from the external environment of the system such that the internal and external environments of the system do not interact or have minimized interactions.

In this disclosure, the term "aseptic" can refer to the absence of microorganisms.

In this disclosure, the term "sterile" can refer to the absence of all microorganisms.

References to specific examples, use of "i.e.," use of the word "invention," etc., are not meant to invoke exception (b) or otherwise restrict the scope of the recited claim terms. Other than situations where exception (b) applies, nothing contained in this document should be considered a disclaimer or disavowal of claim scope.

The subject matter recited in the claims is not coextensive with and should not be interpreted to be coextensive with any embodiment, feature, or combination of features shown in this document. This is true even if only a single embodiment of the feature or combination of features is illustrated and described in this document. Thus, the appended claims should be given their broadest interpretation in view of the prior art and the meaning of the claim terms.

Spatial or directional terms, such as "left," "right," "front," "back," "top," "bottom," and the like, relate to the subject matter as it is shown in the drawings. However, it is to be understood that the described subject matter can assume various alternative orientations and, accordingly, such terms are not to be considered as limiting.

Articles such as "the," "a," and "an" can connote the singular or plural. Also, the word "or" when used without a preceding "either" (or other similar language indicating that "or" is unequivocally meant to be exclusive e.g., only one of x or y, etc.) shall be interpreted to be inclusive (e.g., "x or y" means one or both x or y).

The term "and/or" shall also be interpreted to be inclusive (e.g., "x and/or y" means one or both x or y). In situations where "and/or" or "or" are used as a conjunction for a group of three or more items, the group should be interpreted to include one item alone, all the items together, or any combination or number of the items. Moreover, terms used in the specification and claims such as have, having, include, and including should be construed to be synonymous with the terms comprise and comprising.

Unless otherwise indicated, all numbers or expressions, such as those expressing dimensions, physical characteristics, and the like, used in the specification (other than the claims) are understood to be modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

All disclosed ranges are to be understood to encompass and provide support for claims that recite any and all subranges or any and all individual values subsumed by each range. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

All disclosed numerical values are to be understood as being variable from 0-100% in either direction and thus provide support for claims that recite such values or any and all ranges or subranges that can be formed by such values. For example, a stated numerical value of 8 should be understood to vary from 0 to 16 (100% in either direction) and provide support for claims that recite the range itself (e.g., 0 to 16), any subrange within the range (e.g., 2 to 12.5) or any individual value within that range (e.g., 15.2).

The operations presented in this document are not inherently related to any particular apparatus. Various general-purpose systems can also be used in accordance with the teachings in this document, or it can prove convenient to construct more specialized apparatuses to perform the required method steps. The required structure for a variety of these systems will be apparent to those of skill in the art, along with equivalent variations.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same can also be varied in many ways. Such variations are not to be regarded as a departure from the disclosure, and all such modifications are intended to be included within the scope of the disclosure.

What is claimed is:

1. A product delivery device, comprising:
    a three-piece cap, the three-piece cap comprising:
        a first piece comprised of
            an inlet port;
            a conical section including a wide end and a narrow end; and
            an outlet port disposed flush with the narrow end of the conical section extending away from the conical section; and
        a second piece comprising a securement feature configured to couple the wide end of the conical section to a container; and
        a third piece comprising a gasket, the gasket including an internal angle based at least in part on an angle of the conical section, wherein the first piece engages with the second piece to deform the gasket when connected to the container.

2. The product delivery device of claim 1, wherein walls of the conical section extend from the wide end to the narrow end and define the angle of the conical section.

3. The product delivery device of claim 2, wherein the angle of the conical section varies along a circumference of the narrow end or the wide end.

4. The product delivery device of claim 2, wherein the angle of the conical section is uniform along a circumference of the narrow end or the wide end.

5. The product delivery device of claim 1, wherein the securement feature comprises threads configured to engage an external surface of the container.

6. The product delivery device of claim 1, wherein the product delivery device comprises at least one of polyethylene, polypropylene, polystyrene, polycarbonate, or silicone.

7. The product delivery device of claim 1, wherein the inlet port comprises an inlet port external barb and the outlet port comprises an outlet port external barb.

* * * * *